United States Patent [19]

Breitkopf et al.

[11] Patent Number: 5,008,473

[45] Date of Patent: Apr. 16, 1991

[54] PROCESS FOR PURIFYING PROPANEDIOL-1,3

[75] Inventors: Norbert Breitkopf, Oberhausen; Georg Dämbkes, Dinslaken; Hanswilhelm Bach, Duisburg, all of Fed. Rep. of Germany

[73] Assignee: Ruhrchemie Aktiengesellschaft, Fed. Rep. of Germany

[21] Appl. No.: 98,047

[22] Filed: Sep. 17, 1987

[30] Foreign Application Priority Data

Sep. 24, 1986 [DE] Fed. Rep. of Germany ....... 3632397

[51] Int. Cl.$^5$ .................... C07C 29/86; C07C 31/20
[52] U.S. Cl. .................................................. 568/868
[58] Field of Search .......................................... 568/868

[56] References Cited

U.S. PATENT DOCUMENTS 2,154,930 4/1939 Evans ................................. 568/868

FOREIGN PATENT DOCUMENTS 2029560 12/1971 Fed. Rep. of Germany ...... 568/868
64204 5/1975 Japan ................................. 568/868

*Primary Examiner*—J. E. Evans
*Attorney, Agent, or Firm*—Jordan B. Bierman

[57] ABSTRACT

A process for the purification of propanediol-1,3, especially when produced by hydration of acrolein with water, including extracting the diol with cyclohexane. Preferably, from 2 to 10 parts by weight of cyclohexane per part by weight of diol is used. The purification is usually carried out below 60° C.

5 Claims, No Drawings

PROCESS FOR PURIFYING PROPANEDIOL-1,3

This application claims the priority of German P 36 32 397.7, filed Sept. 24, 1986.

The invention relates to a process for purifying propanediol, especially when obtained by hydrating acrolein with water followed by hydrogenation of the 3-hydroxypropanal formed as a primary product. In order to remove unwanted by-products, the diol is treated with cyclohexane.

BACKGROUND OF THE INVENTION

Propanediol-1,3 is a valuable intermediate product which is used particularly in connection with solvents and plastics.. Industrial scale production is mainly carried out by the catalytic hydration of acrolein with water (see U.S. Pat. No. 2,434,110). An aqueous solution of acrolein is mixed with enough acid to achieve a pH value of from about 0.5 to about 7. In the presence of an anti-oxidant, e.g. hydroquinone, the mixture is heated for 0.5 to 8 hours to temperatures not exceeding 100° C. The reaction mixture is then hydrogenated in the presence of Raney nickel. Variations or further developments of this process relate to the use of ion exchangers as catalysts for the addition of water (see U.S. Pat. No. 3,536,763) and the hydrogenation of the 3-hydroxypropanal in an organic solvent, e.g. isobutanol, in the presence of nickel carrier catalysts (see DE-PS 20 54 601). Through repeated distillation, propanediol-1,3 with a degree of purity of more than 99% is obtained from the hydrogenation product.

However, even after careful distillation turbidity may occur in the pure propanediol-1,3. It is believed to result from the quality, of the acrolein used. By diene synthesis, 2-formyl-2,3-dihydro-gamma-pyrane (dimeric acrolein) can form from 2 molecules of acrolein, the former reacting with propanediol-1,3 forming the hemiacetal and acetal. These aldehyde derivatives are the cause of the turbidity. In some cases, they even impair the further processing of the diol.

OBJECT OF THE INVENTION

The problem was to develop a process of reliably removing the contaminants causing turbidity from the diol.

DESCRIPTION OF THE INVENTION

The invention consists in a process for purifying propanediol-1,3, especially that obtained by hydrating acrolein with water. It is characterized in that the diol is extracted with cyclohexane. With the aid of the new procedure a pure propanediol-1,3 can be obtained which is free of turbidity and satisfies even the highest demands placed on purity.

It was not to be expected that the purification of diol by simple extraction in a selected solvent would lead to such excellent results. Attempts to solve the problem by fine distillation were a failure, as were attempts to extract with a wide variety of aliphatic, cycloaliphatic and aromatic hydrocarbons under various conditions. Surprisingly, cyclohexane proved to be an extremely suitable extracting agent. It is of particular importance that the two phases, diol and hydrocarbon, can be very easily separated from one another after extraction, and that traces of the extracting agent remaining in the extraction product can be easily removed by vaporization. The solubility of propanediol-1,3 in cyclohexane is so low that hardly any diol is lost.

In practice, propanediol-1,3 is purified by countercurrent extraction, one single extraction stage generally being sufficient. In rare cases it may be necessary to extract in several stages by countercurrent or crosscurrent extraction. About 2 to 10 parts by weight, preferably 4 to 6 parts by weight, of extracting agent are used per part by weight of diol. The contaminants are separated from the diol at a temperature below 60° C., preferably from 20° C. to 60° C., and especially at 30° C. to 50° C. After purification, the cyclohexane contained in the diol is removed by vaporization, advantageously in a vacuum at 50 to 150 hPa. The new process provides qualitatively excellent propanediol-1,3 which is clear and odorless.

The new procedure is explained in more detail by the following examples:

EXAMPLE 1

100 g of turbid propanediol-1,3 are mixed intensively with 5 g of cyclohexane in a stirring flask at room temperature. After separation of the phases, which takes more than one hour, a clear diol phase is obtained. It is freed from the remaining cyclohexane at 100° C. in a vacuum (about 100 hPa). 99 g of transparent and odorless propanediol-1,3 remain.

EXAMPLE 2

Example 1 is repeated, but the operating temperature raised to 50° C. Under these conditions phase separation takes place in a few minutes. When the purification as described in Example 1 is complete, 99 g of transparent and odorless product is obtained.

EXAMPLE 3 and 4

Example 1 is repeated using i-octane and toluene as extracting agents. The results are shown in the following Table.

|  | Example No. | |
| --- | --- | --- |
|  | 3 | 4 |
| Extracting agent | i-octane | toluene |
| Propanediol yield | 98% | 99% |
| Propanediol quality | turbid | turbid |

EXAMPLES 5 and 6

Examples 3 and 4 are repeated at an increased operating temperature of 50° C. The results are shown in the follow Table.

|  | Example No. | |
| --- | --- | --- |
|  | 5 | 6 |
| Extracting agent | i-octane | toluene |
| Propanediol yield | 99% | 99% |
| Propanediol quality | turbid | turbid |

What we claim is:

1. A process for the purification of turbid propanediol-1,3, produced by hydration of acrolein with water followed by hydrogenation, said process comprising extracting said diol with cyclohexane.

2. The process of claim 1 wherein there are 2 to 10 parts by weight of cyclohexane per part by weight of said diol.

3. The process of claim 2 wherein there are 4 to 6 parts by weight of cyclohexane per part by weight of said diol.

4. The process of claim 1 wherein said purification is carried out below about 60° C.

5. The process of claim 3 wherein said purification is carried out from about 20° C. to about 60° C.